(12) United States Patent
Deshpande et al.

(10) Patent No.: US 7,098,329 B2
(45) Date of Patent: Aug. 29, 2006

(54) PROCESS FOR THE PREPARATION OF A CEPHALOSPORIN ANTIBIOTIC

(75) Inventors: Pandurang Balwant Deshpande, Sholinganallur (IN); Prabhat Kumar Sahoo, Sholinganallur (IN); Anandam Vempali, Sholinganallur (IN); Srinivasu Ghanta, Sholinganallur (IN)

(73) Assignee: Orchid Chemicals & Pharmaceuticals Ltd., Chennai (IN)

( * ) Notice: Subject to any disclaimer, the term of this patent is extended or adjusted under 35 U.S.C. 154(b) by 97 days.

(21) Appl. No.: 10/867,723

(22) Filed: Jun. 16, 2004

(65) Prior Publication Data

US 2005/0027118 A1    Feb. 3, 2005

(30) Foreign Application Priority Data

Jun. 19, 2003    (IN)    ........................ 501/MAS/2003

(51) Int. Cl.
*C07D 501/36*    (2006.01)
(52) U.S. Cl. ..................................... 540/227
(58) Field of Classification Search ................ 540/227
See application file for complete search history.

(56) References Cited

U.S. PATENT DOCUMENTS

| 4,423,213 | A | * | 12/1983 | Takaya et al. | 540/215 |
| 4,427,674 | A | * | 1/1984 | Takaya et al. | 514/202 |
| 4,935,507 | A | * | 6/1990 | Takaya et al. | 540/222 |
| 5,109,131 | A | * | 4/1992 | Naito et al. | 540/227 |
| 6,384,215 | B1 | * | 5/2002 | Deshpande et al. | 540/227 |
| 6,458,949 | B1 | * | 10/2002 | Handa et al. | 540/226 |
| 6,552,186 | B1 | * | 4/2003 | Gerlach et al. | 540/222 |
| 2004/0132995 | A1 | * | 7/2004 | Deshpande et al. | 540/222 |
| 2005/0059820 | A1 | * | 3/2005 | Datta et al. | 540/227 |
| 2005/0059821 | A1 | * | 3/2005 | Datta et al. | 540/227 |
| 2005/0065316 | A1 | * | 3/2005 | Sikes | 528/322 |
| 2005/0080070 | A1 | * | 4/2005 | Deshpande et al. | 514/202 |
| 2005/0119478 | A1 | * | 6/2005 | Monguzzi et al. | 540/227 |

FOREIGN PATENT DOCUMENTS

| EP | 30294 | A2 | * | 6/1981 |
| EP | 556768 | A2 | * | 8/1993 |
| EP | 842937 | A2 | * | 5/1998 |

* cited by examiner

*Primary Examiner*—Mark L. Berch
(74) *Attorney, Agent, or Firm*—Oliff & Berridge, PLC

(57) ABSTRACT

An improved process for the preparation of ceftriaxone sodium comprising the steps of:
i) reacting the 3-cephem derivative of formula (II)

(II)

with halo acid derivative of formula (III)

(III)

wherein X represents halogen and Y represent halogen in the presence of silylating agent and methylene chloride at −25 to 10° C., to produce (IV), (IV)

ii) quenching the reaction by pouring the reaction mixture into water or in a aqueous solution of sodium carbonate,
iii) preparing sodium salt solution of (IV) by adding sodium carbonate and separating the organic layer,
iv) cyclizing the sodium salt of (IV) in the aqueous solution with thiourea at a temperature in the range of 0 to 30° C.,
v) adjusting the pH to 1.5 to 2.5 to precipitate the ceftriaxone free acid,
vi) converting the ceftriaxone free acid to sodium salt using sodium-2-ethyl hexanoate in water and
vii) precipitating and isolating the ceftriaxone sodium.

5 Claims, No Drawings

US 7,098,329 B2

PROCESS FOR THE PREPARATION OF A CEPHALOSPORIN ANTIBIOTIC

FIELD OF THE INVENTION

The present invention relates to an improved process for the preparation of a cephalosporin antibiotic. More particularly, the present invention relates to an improved process for the preparation of ceftriaxone sodium of the formula (I).

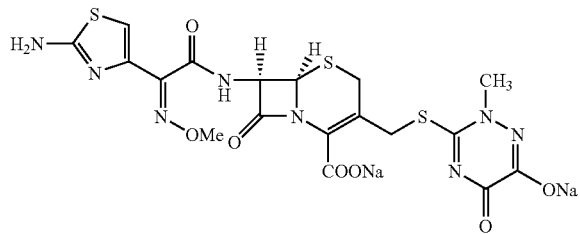

BACKGROUND OF THE INVENTION

Ceftriaxone is chemically known as (6R,7R)-7-[[(Z)-2-(2-aminothiazol-4-yl)-2-methoxyimino]acetamido]-3-(2,5-dihydro-6-hydroxy-2-methyl-5-oxo-1,2,4-triazin-3-yl)thiomethyl-3-cephem-4-carboxylic acid disodium salt hemiheptahydrate.

Ceftriaxone is a cephalosporin antibiotic of a great therapeutic interest due to its effective antibacterial activity in the treatment of several affections and is disclosed in U.S. Pat. No. 4,758,556.

EP 0037 380 describes a process for the preparation of ceftriaxone which starts from 7-amino-3-(2,5-dihydro-6-hydroxy-2-methyl-5-oxo-1,2,4-triazin-3-yl)thiomethyl-3-cephem-4-carboxylic acid, which suitably protected at the carboxylic group, is made to react with 2-mercaptobenzothiazole 2-(2-aminothiazol-4-yl)-2-synmethoxymino acetate, then, after being deprotected, it gives ceftriaxone in the form of free acid. Its corresponding transformation into its soluble form as disodium salt is carried out afterwards according to the known techniques.

U.S. Pat. No. 6,552,186 claims a process for the preparation of ceftriaxone which comprises reacting of 7-amino-3-{[(2,5-dihydro-6-hydroxy-2-methyl-5-oxo-as-triazin-3-yl)thio]methyl)}-3-cephem-4-carboxylic acid with 4-halo-2 (Z)-methoximino-3-oxobutyric acid using a silylating agent in the presence of solvent at a temperature of −10° C. to produce silylated compound and cyclizing the silylated compound with silylated thiourea using a solvent system containing organic solvent and water to obtain ceftriaxone formula (I). This patent also claims a process wherein the silylated (6R,7R)-7-[4-halo-2-[methoxyimino]acetamido]-3-[[(2,5-dihydro-6-hydroxy-2-methyl-5-oxo-1,2,4-triazin-3-yl)thio]methyl]-3-cephem-4-carboxylic acid is desilylated and then reacted with thiourea to produce ceftriaxone of formula (I).

EP 30294 disclosed a process comprising reacting 7-amino-3-{[(2,5-dihydro-6-hydroxy-2-methyl-5-oxo-as-triazin-3-yl)thio]methyl)}-3-cephem-4-carboxylic acid with 4-halo-2(Z)-methoximino-3-oxobutyric acid in the presence of a silylating agent in the presence of solvent to produce (6R,7R)-7-[4-halo-2-[methoxyimino]acetamido]-3-[[(2,5-dihydro-6-hydroxy-2-methyl-5-oxo-1,2,4-triazin-3-yl)thio]methyl]-3-cephem-4-carboxylic acid and reacting with thiourea in the presence of solvent selected from lower alkanol, lower ketone, an ether, DMF, DMAc, water and the like or mixtures thereof to produce ceftriaxone free acid which is then converted to sodium salt of formula (I).

The above-mentioned processes produce ceftriaxone using multi solvent system, which makes the recovery of solvents difficult and also increases the production cost. We focused our research to replace the multi solvent system with single organic solvent in order to reduce the cost of production and improve the purity and yield of the product. Overall, the process is environment friendly because, the solvent used is easily recovered and reused without producing much effluent.

The present invention is based on our observation that the purity and yield of the product can be improved when the reaction is carried out in water as a solvent alone without using multiple solvents.

OBJECTIVE OF THE INVENTION

The main objective of the present invention is to provide an improved process for the preparation of ceftriaxone of the formula (I), which avoids the use of multi solvent system.

Another objective of the present invention is to provide an improved process for the preparation of ceftriaxone of the formula (I) in high purity and yield.

Another objective of the present invention is to provide an environmental friendly process for the preparation of ceftriaxone of the formula (I).

Another objective of the present invention is to provide a cost effective process by way of limited usage of organic solvents.

SUMMARY OF THE INVENTION

Accordingly, the present invention provides an improved process for the preparation of ceftriaxone sodium of formula (I),

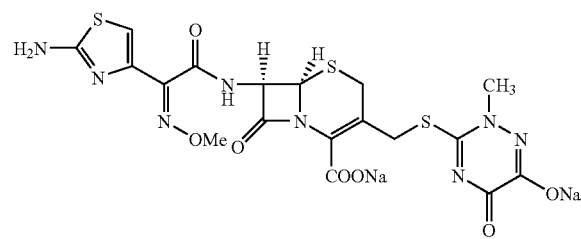

which comprises the steps of:
i) reacting the 3-cephem derivative of formula (II) with halo acid derivative of formula (III) wherein X represents halogen atom and Y represent a halogen atom or an activating groups in the presence of a silylating agent and methylene chloride at a temperature in the range of −25 to 10° C., to produce compound of formula (IV),
ii) quenching the reaction by pouring the reaction mixture into water or in an aqueous solution of sodium carbonate,
iii) preparing sodium salt solution of compound of formula (IV) by adding sodium carbonate and separating the organic layer,
iv) cyclizing the sodium salt of compound of formula (IV) in the aqueous solution with thiourea at a temperature in the range of 0 to 30° C., v) adjusting the pH to 1.5 to 2.5 to precipitate the ceftriaxone free acid,
vi) converting the ceftriaxone free acid to sodium salt using sodium-2-ethyl hexanoate in water and
vii) precipitating and isolating the ceftriaxone sodium of formula (I) using a solvent.

The reaction is shown in scheme I given below:

Scheme-I

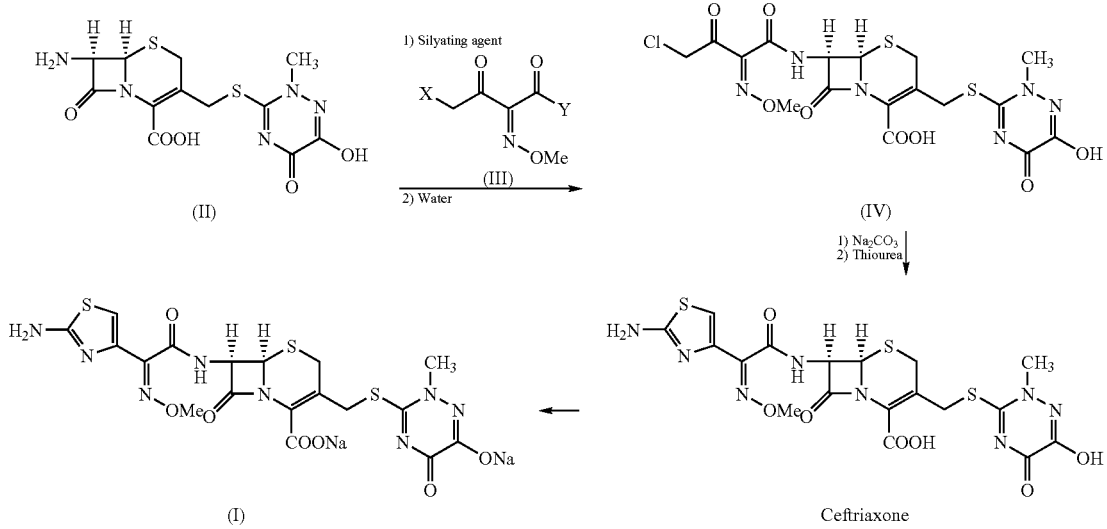

In yet another embodiment of the present invention, the solvent used for isolation of ceftriaxone of compound of formula (I) is selected from acetone, ethyl acetate and the like.

In an embodiment of the present invention, the purity of ceftriaxone obtained is >99% and assay is >98%.

In an embodiment of the present invention, the compound of formula (I) obtained is a syn-isomer.

The use of water alone for cyclization of compound of formula (IV) with thiourea, makes the process cost effective process and environment friendly. The water can be removed easily from the product without much effort thus making the process free from the tedious and time-consuming process of solvent recovery.

The process is environment friendly as it avoids the use of organic solvents.

The present invention is provided by the example given below, which is provided by way of illustration only and should not be considered to limit the scope of the invention.

DETAILED DESCRIPTION OF THE INVENTION

In an embodiment of the present invention, the groups represented by Y are selected from halogen atom such as chlorine, bromine or activating groups such as

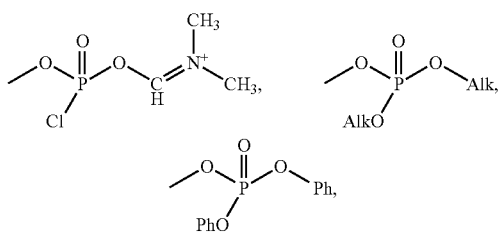

where Alk group represents $(C_1-C_4)$alkyl group such as methyl, ethyl, n-propyl, iso-propyl, n-butyl or iso-butyl.

In an embodiment of the present invention the silylating agent is selected from hexamethyldisilazane (HMDS), trimethylchlorosilane (TMCS), trimethylsilyl iodide (TMSI), N,O-bis-(trimethylsilyl)-acetamide (BSA), methyltrimethylsilyltrifluoroacetamide (MSTFA), N,O-bistrimethylsilyltrifluoroacetamide (BSTFA), methyldichlorosilane, dimethyldichlorosilane, diphenyldichlorosilane, N-methylsilylacetamide (MSA), bistrimethylsilylurea and the like.

In yet another embodiment of the present invention, the compound of formula (II) and silylating agent is used in the ratio of 1:1.5 to 1:2.5.

EXAMPLE 1

Preparation of (6R,7R)-7-[[(Z)-2-(2-aminothiazol-4-yl)-2-methioxyimino]acetamidol]-3-(2,5-dihydro-6-hydroxy-2-methyl-5-oxo-1,2,4-triazin-3-yl)thiomethyl-3-cephem-4-carboxylic acid disodium (ceftriaxone sodium)

7-Amino-3-(2,5-dihydro-6-hydroxy-2-methyl-5-oxo-1,2,4-triazin-3-yl)thiomethyl-3-cephem-4-carboxylic acid (25 g) was stirred with BSA (45 g) in methylene chloride (300 mL) at 35–40° C. for 1 hour 30 minutes to get a clear solution. The solution was cooled to −10° C. and to this was added a pre-cooled solution of 4-chloro-2(Z)-methoxy-imino-3-oxo-butyric acid chloride prepared by stirring 4-chloro-2(Z)-methoxyimino-3-oxo-butyric acid (14.5 g) and phosphorus pentachloride (16.8 g) in methylene chloride (100 mL) at −10° over 1 hour. The reaction mixture was stirred for 15 minutes, poured into chilled water (250 mL)

and stirred at 4–7° C. for 1 hour during which time a solid separated out. The pH of the solution was adjusted to 5–6 with saturated sodium carbonate solution upon which the solid dissolves completely. The resulting two layers were separated. The aqueous layer was charcoalised at 20–25° C. for 15 minutes, filtered and thiourea (10.2 g) was added to this and the reaction mixture was stirred at 20–25° C. for 4 hours while maintaining the pH at 5.5 to 5.7 with sodium carbonate solution. The clear solution was treated with activated charcoal at 25° C., filtered and pH brought down to 1.8–2.0 with dilute hydrochloric acid at 5–6° C. The precipitated solid was filtered, washed with water thoroughly and the total weight of the material was made up to 130 g by adding water. To this wet slurry was added a solution of sodium-2-ethyl hexanoate (34 g) in acetone (70 mL) to get a clear solution, which is treated with activated charcoal, filtered, and acetone (450 mL) was added and cooled to −10° C., upon which, some coloured sticky material precipitates out and sticks to the wall of the flask. The supernatant solution was decanted out, temperature was raised to 18–20° C. and acetone (800 mL) was added slowly to precipitate out the white ceftriaxone sodium. The product was stirred for 1.5 hour at 18–20° C., filtered and dried to get 22 g of the product with chromatographic purity of 99.8% and content above 97%).

EXAMPLE 2

Preparation of Ceftriaxone Sodium

7-Amino-3-(2,5-dihydro-6-hydroxy-2-methyl-5-oxo-1,2,4-triazin-3-yl)thiomethyl-3-cephem-4-carboxylic acid (25 g) was stirred with BSU (61.75 g) in methylene chloride (300 mL) at 35–40° C. for 5 hours. The suspension was cooled to −15° C. and to this was added a pre-cooled solution of 4-chloro-2(Z)-methoxyimino-3-oxo-butyric acid chloride prepared by stirring 4-chloro-2(Z)-methoxyimino-3-oxo-butyric acid (15.72 g) and phosphorus pentachloride (16.8 g) in methylene chloride (200 mL) at −15° C. over 1 hour. The reaction mixture was stirred for 15 minutes, poured into an aqueous solution of sodium carbonate (16 g) in 375 mL of water at 4–7° C. The pH of the reaction mixture was adjusted to 5.8–6 by adding sodium carbonate solution and the resulting two layers were separated. To the aqueous layer was added thiourea (10.2 g) and the reaction mixture was stirred at 12–15° C. for 8–10 hours while maintaining the pH at 5.5 to 5.7 with sodium carbonate solution. The clear solution was washed with methylene chloride and treated with activated charcoal and finally acidified with dilute hydrochloric acid to pH 2.5 at 5–6° C. The precipitated solid was filtered, washed with water thoroughly and the total weight of the material was made up to 160 g by adding water. To this was added an aqueous solution of sodium-2-ethyl hexanoate (20.12 g) in water (25 mL) at 10–15° C. to get a clear solution. To this solution was added acetone (1200 mL) slowly to precipitate out the product. The product was stirred for 1.5 hours at 18–20° C., filtered and dried to get 30 g of ceftriaxone sodium with purity of more than 99%.

We claim:

1. An improved process for the preparation of ceftriaxone sodium of formula (I),

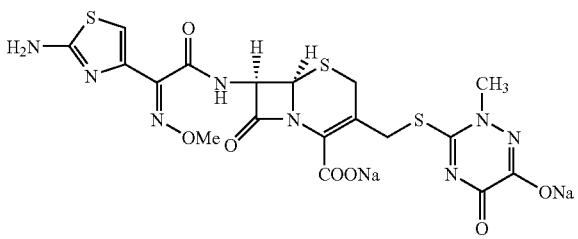

which comprises the steps of:
i) reacting the 3-cephem derivative of formula (II)

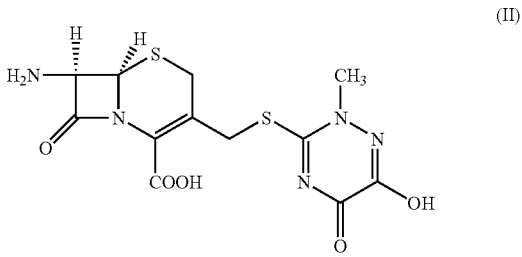

with halo acid derivative of formula (III)

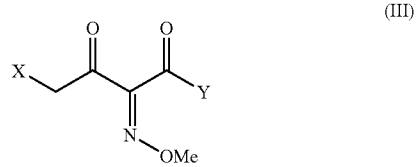

wherein X represents halogen atom and Y represent a halogen atom or an activating groups in the presence of a silylating agent and methylene chloride at a temperature in the range of −25 to 10° C.,
ii) quenching the reaction by pouring the reaction mixture into water or in a solution of sodium carbonate in water, to produce a compound of formula (IV),

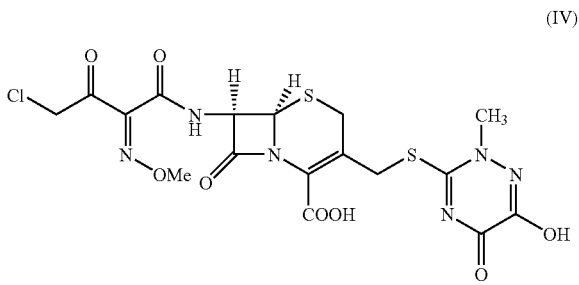

iii) preparing sodium salt solution of the compound of formula (IV) by adding sodium carbonate and separating the organic layer,
iv) cyclizing the sodium salt of the compound of formula (IV) in the water solution with thiourea at a temperature in the range of 0 to 30° C.,
v) adjusting the pH to 1.5 to 2.5 to precipitate the ceftriaxone free acid, vi) converting the ceftriaxone free acid to sodium salt using sodium-2-ethyl hexanoate in water and vii) precipitating and isolating the cefiriaxone sodium of formula (I) using a solvent.

2. The process as claimed in claim 1, wherein the group represented by Y is selected from halogen selected from chlorine or bromine.

3. The process as claimed in claim 1, the silylating agent used is selected from hexamethyldisilazane (HMDS), trimethylchlorosilane (TMCS), trimethylsilyl iodide (TMSI), N,O-bis-(trimethylsilyl)-acetamide (BSA), methyltrimethylsilyltrifluoroacetamide (MSTFA), N,O-bistrimethylsilyltrifluoroacetamide (BSTFA), methyldichlorosilane, dimethyldichlorosilane, diphenyldichlorosilane, N-methylsilylacetamide (MSA) or bistrimethylsilylurea (BSU).

4. The process as claimed in claim 1, the compound of formula (II) and silylating agent is used in the ratio of 1:1.5 to 1:2.5.

5. The process as claimed in claim 1, wherein the solvent used for isolation in step (vii) is selected from acetone or ethyl acetate.

* * * * *